United States Patent [19]

Creswell et al.

[11] Patent Number: 5,162,360

[45] Date of Patent: Nov. 10, 1992

[54] 2-HETEROATOM CONTAINING UREA AND THIOUREA ACAT INHIBITORS

[75] Inventors: Mark W. Creswell, Chelsea; Andrew D. White, Lakeland, both of Mich.

[73] Assignee: Warner-Lambert Company, Morris Plains, N.J.

[21] Appl. No.: 719,878

[22] Filed: Jun. 24, 1991

[51] Int. Cl.$^5$ ............... A61K 31/495; C07D 277/04; C07D 401/00; C07D 413/00
[52] U.S. Cl. ..................... 514/371; 548/196; 546/187; 546/209; 544/367; 544/357; 514/316; 514/326; 514/252
[58] Field of Search ............. 548/196; 546/187, 209; 544/367, 357; 514/252, 316, 326, 371

[56]  References Cited

U.S. PATENT DOCUMENTS

| | | | |
|---|---|---|---|
| 3,551,442 | 12/1970 | Guillot et al. | 548/196 |
| 3,821,239 | 6/1974 | Guillot et al. | 260/306 |
| 4,405,644 | 9/1983 | Kabbe et al. | 31/275 |

OTHER PUBLICATIONS

*J. Med. Chem.*, 1979, vol. 22, No. 1, R. K. Y. Zee--Cheng et al., "Antileukemic Activity of Substituted Ureidothiazoles, Ureidothiadiazoles, and Related Compounds".

*Primary Examiner*—Mary C. Lee
*Assistant Examiner*—Robert C. Whittenbaugh
*Attorney, Agent, or Firm*—Ruth H. Newtson; Ronald A. Daignault

[57]  ABSTRACT

The present invention provides N-substituted aryl-N'-heterocyclic substituted ureas and thioureas of the formula

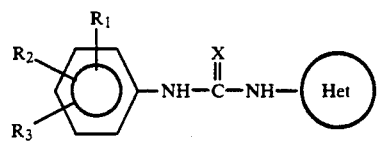

wherein $R_1$, $R_2$ and $R_3$ are hydrogen, fluorine, chlorine, bromine, alkyl, alkoxy, substituted or unsubstituted benzoyl, substituted or unsubstituted phenyl, amino, substituted amino, or a monocyclic heterocyclic, or a carboxy group; and Het is a substituted monocyclic heterocyclic group containing two hetero atoms selected from nitrogen, oxygen or sulfur; which are useful in treating hypercholesterolemia and atherosclerosis.

5 Claims, No Drawings

2-HETEROATOM CONTAINING UREA AND THIOUREA ACAT INHIBITORS

BACKGROUND OF THE INVENTION

This invention relates to chemical compounds having pharmacological activity, to pharmaceutical compositions which include these compounds, and to a pharmaceutical method of treatment. More particularly, this invention concerns certain 2-heteroatom aryl ureas and thioureas which inhibit the enzyme acyl-coenzyme A:-cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention provides N-substituted aryl N'-heterocyclic substituted ureas and thioureas which are inhibitors of acyl-CoA: cholesterol acyltransferase (ACAT). More particularly, the present invention provides ACAT inhibitors wherein the acyl moiety is a substituted phenyl group and the heterocyclic moiety is a monocyclic heterocyclic group containing 2-hetero atoms selected from nitrogen, oxygen, and sulfur. The compounds of the present invention may be depicted by the following Formula I

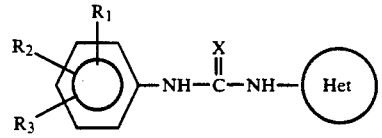

Formula I wherein
X is oxygen or sulfur;
wherein each of $R_1$, $R_2$, and $R_3$ is the same or different and is selected from
hydrogen,
fluorine,
chlorine,
bromine,
a straight or branched alkyl group having from one to six carbon atoms,
a straight or branched alkoxy group having from one to six carbon atoms,
benzoyl which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms,
benzyl which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms,
phenyl which is unsubstituted or is substituted with from one to three substituents selected from fluorine, chlorine, bromine, iodine, a straight or branched alkyl group having from one to six carbon atoms, or a straight or branched alkoxy group having from one to six carbon atoms;
$NR_4R_5$ wherein each of $R_4$ and $R_5$ is the same or different and is hydrogen, a straight or branched alkyl group having from one to four carbon atoms or —$NR_4R_5$ taken together form a monocyclic heterocyclic group selected from pyrrolidino, piperidino, piperazino, or piperazino substituted on the 4-position with a straight or branched alkyl group having from one to four carbon atoms;
—$COR_6$ wherein $R_6$ is hydroxy, a straight or branched alkoxy group having from one to six carbon atoms, benzyloxy which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms, or $R_6$ is —$NR_4R_5$ wherein $R_4$ and $R_5$ have the meanings defined above;
wherein Het is selected from

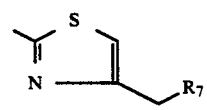

(1)

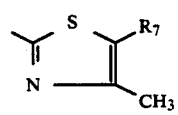

(2)

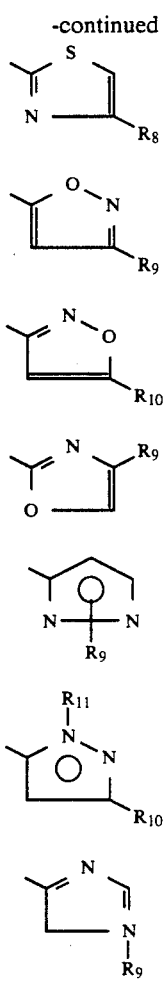

wherein $R_7$ is hydrogen or straight or branched alkyl having from 1 to 14 carbon atoms;

wherein $R_8$ is phenyl;

wherein $R_9$ is straight or branched alkyl having from 1 to 16 carbon atoms;

wherein $R_{10}$ is $R_9$ or the group —$CH_2NR_aR_a$ wherein each $R_a$ is an alkyl group of from 1 to 10 carbon atoms;

wherein $R_{11}$ is benzyl, 2-pyridyl or hydrogen; and pharmaceutically acceptable salts and isomers thereof.

DETAILED DESCRIPTION OF INVENTION

Pharmaceutically acceptable salts of the compounds of Formula I are also included as a part of the present invention.

The acid addition salts may be generated from the free base forms of the compounds by reaction of the latter with one equivalent of a suitable nontoxic, pharmaceutically acceptable acid, followed by evaporation of the solvent employed for the reaction and recrystallization of the salt, if required. The free base may be recovered from the acid addition salt by reaction of the salt with a water solution of the salt with a suitable base such as sodium carbonate, sodium bicarbonate, potassium carbonate, sodium hydroxide, and the like.

Suitable acids for forming acid addition salts of the compounds of this invention include, but are not necessarily limited to acetic, benzoic, benzenesulfonic, tartaric, hydrobromic, hydrochloric, citric, fumaric, glu- conic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well known to practitioners of the pharmaceutical formulation arts. (See, for example, Stephen N. Berge, et al, *J. Pharm. Sciences* 66:1-19 (1977).

The compounds of the present invention may also exist in different stereoisomeric forms by virtue of the presence of one or more asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers in chiral chromatographic columns.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

Preferred compounds of this invention are those wherein Het has the meaning defined in groups 4, 5, and 7 above with the more preferred compounds being those defined in groups 4 and 5. The most preferred compounds are those set forth below as Examples 8 through 17, 19, and 23.

As shown by the data presented in Table 1, the compounds of the present invention are potent inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described by F. J. Field and R. G. Salone, in *Biochemica et Biophysica* 712:557-570 (1982). The test assesses the ability of a test compound to inhibit the acylation of cholesterol by oleic acid by measuring the amount of radio-labeled cholesterol oleate formed from radiolabeled oleic acid in a tissue preparation containing rabbit intestinal microsomes.

The data appear in Table 1 where they are expressed as $IC_{50}$ values; i.e., the concentration of test compound required to inhibit 50% expression of the enzyme.

TABLE 1

| Compound of Example | $IC_{50}$ ($\mu$M) |
|---|---|
| 1 | 0.12 |
| 2 | 0.15 |
| 3 | 1.9 |
| 4 | 1.6 |
| 5 | >5 |
| 6 | >5 |
| 7 | >1 |
| 8 | 0.019 |
| 9 | 0.027 |
| 10 | 0.029 |
| 11 | 0.020 |
| 12 | 0.013 |
| 13 | 0.028 |
| 14 | 0.028 |
| 15 | 0.027 |
| 16 | 0.014 |
| 17 | 0.11 |
| 18 | >5 |
| 19 | 0.51 |
| 20 | 2.7 |

TABLE 1-continued

| Compound of Example | IC$_{50}$ ($\mu$M) |
| --- | --- |
| 22 | 1.9 |
| 23 | 0.035 |
| 24 | 0.1 |

In one in vivo screen designated APCC, male Sprague-Dawley rats (200 to 225 g) were randomly divided into treatment groups and dosed orally at 4 PM with either vehicle (CMC/Tween) or suspensions of test compounds in vehicle. The control group received vehicle alone. Immediately after dosing, all animals received ad libitum a chow diet supplemented with peanut oil (5.5%), cholesterol (1.5%), and cholic acid (0.5%). The next day the animals were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2. The figure in parenthesis indicates the number of milligrams/kilogram of test compound administered.

TABLE 2

| Compound of Example | % Change (mg/dl) |
| --- | --- |
| 1 | −20 (30) |
| 3 | −17 (30) |
| 4 | +4 (30) |
| 8 | −61 (30) |
|   | −58 (3) |
| 9 | −67 (30) |
|   | −54 (3) |
| 10 | −69 (30) |
|   | −61 (3) |
| 11 | −70 (30) |
|   | −67 (3) |
| 12 | −62 (30) |
|   | −51 (3) |
| 13 | −64 (30) |
|   | −44 (3) |
| 14 | −62 (30) |
|   | −29 (3) |
| 15 | −61 (30) |
|   | −51 (3) |
| 16 | −62 (30) |
|   | −59 (3) |
| 17 | −58 (30) |
|   | −47 (3) |
| 19 | −50 (30) |
|   | −33 (3) |
| 20 | −7 (30) |
| 22 | −9 (30) |
| 23 | −64 (30) |
|   | +5 (3) |
| 24 | +9 (30) |

In therapeutic use as agents for treating hypercholesterolemia or atherosclerosis, the compounds of Formula I are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of Formula I are prepared in various ways. In reading the description which follows, one should refer to flow chart hereof wherein the chemical schemes are depicted. The thiazole containing compounds of Formula I wherein Het is group (1) or (2) are prepared as set forth in Scheme I of the Flow Charts. The thiazoles of formulas (e) and (f) are prepared from the amines (c) and (d) which are obtained via treatment of an $\alpha$-haloketone (b') with thiourea. In situ iodination gives a mixture of iodides resulting in the two aminothiazoles (c) and (d) which are readily separated by chromatography. The preparation of thiazole-containing compounds of Formula I wherein Het is group (3) is depicted in Scheme II of the Flow Charts. This route of synthesis may also be used to prepare compounds of Formula I wherein Het is group (1) and R$_7$ is a lower alkyl group. The amine (h) is commercially available or is prepared from the commercially available ketohalide (g) by reaction with thiourea. In Schemes I and II the various substituent groups $R_1$, $R_2$, $R_3$, $R_7$, $R_8$, and X have the meanings defined in Formula I.

The isoxazole containing compounds of Formula I wherein Het is group (4) or (5) and wherein $R_9$ and $R_{10}$ are straight or branched alkyl groups having from 1 to 16 carbon atoms are prepared as depicted in Scheme III in the Flow Chart wherein $R_{12}$ is an alkyl group of from 1 to 16 carbon atoms being straight or branched, and $R_1$, $R_2$, $R_3$, and X have the meanings defined in Formula I. As depicted in Scheme III the isoxazole ureas (m) and (n) are prepared from a divergent route from the same nitrile (j). The nitrile (j) is commercially available or is prepared by reaction of phenyl cyanate with an appropriate acetylene of the formula $R_{12}C \equiv CH$ wherein $R_{12}$ is as defined above. The required acetylenes are commercially available or can be prepared by known procedures as described for example, in the following review articles: Ben-Efraim in Patai, "The Chemistry of the Carbon-Carbon Triple Bond", pp. 790–800, Wiley, New York, 1978; Ziegenbein, in Viehe, "Acetylenes", pp 185–206, 241–244, Marcel Dekker, New York, 1969. The isoxazole ureas of Formula I wherein Het is group (3) and $R_{11}$ is $-CH_2NR_aR_a$ wherein $R_a$ has the meanings defined in Formula I are prepared as depicted in route (b) of Scheme III only substituting a nitrile of the formula $R_aR_aNCH_2C \equiv CCN$ wherein $R_a$ and $R_b$ are as defined in Formula I for the nitrile of formula (j). The nitrile $R_aR_aNCH_2C \equiv CCN$ is available commercially or can be prepared by reacting aminomethylacetylene, i.e., $H_2NCH_2C \equiv CH$ with an aldehyde of the formula $R_a$—CHO in the presence of sodium cyanoborohydride ($NaBH_3CN$) and hydrochloric acid in a lower alcohol such as ethanol.

The oxazole containing compounds of Formula I wherein Het is group (6) are prepared as shown in Scheme IV of the Flow Chart. The oxazole amine is prepared as shown in Scheme V of the Flow Chart. In Scheme V $R_9$ has the meaning defined in Formula I and the reagents have their known meanings, i.e., LDA is lithium diisopropylamide, TMSCl is trimethylsilylchloride, $H_2NCN$ is cyanamide and $Bu_4NOH$ is tetrabutylammonium hydroxide.

The pyrazole containing compounds of Formula I wherein Het is group (7) are prepared as shown in Scheme VI of the Flow Chart whereby the commercially available 3-aminopyrazole is alkylated then reacted with an appropriate phenylisocyanate or phenylisothiocyanate to give compounds of structure (w) The substituent groups $R_1$, $R_2$, $R_3$, $R_9$, and X have the meanings defined in Formula I. The pyrazole containing compounds of Formula I wherein Het is group (8) are prepared as shown in Scheme VII of the Flow Chart. The commercially available acetylene (x) is treated with phenylcyanate to form the nitrile (y) which is reacted with an appropriate hydrazine which is commercially available to give the substituted pyrazole amine of formula (z) which is reacted with a phenylisocyanate or phenylisothiocyanate to give the formula (aa) compounds. The substituent groups $R_1$, $R_2$, $R_3$, $R_{10}$, $R_{11}$, and X have the meanings defined in Formula I.

The imidazole containing compounds of Formula I wherein Het is the group (9) are prepared as depicted in Scheme VIII of the Flow Chart. The commercially available 4-nitroimidazole (bb) is treated with tetrabutylammonium hydroxide to give the salt (cc) which is reacted with an appropriate halide to give the alkylated nitroimidazole (dd), which is reduced to the amine (ee) and reacted with a phenyl isocyanate or phenyl isothiocyanate to give compounds of formula (ff).

EXAMPLE 1

N-[2,6-bis(1-methylethyl)phenyl]-N'-(5-decyl-4-methyl-2-thiazolyl)urea (a) Preparation of 2-amino-4-methyl-5-decylthiazole (A) and 2-amino-4-undecylthiazole (B)

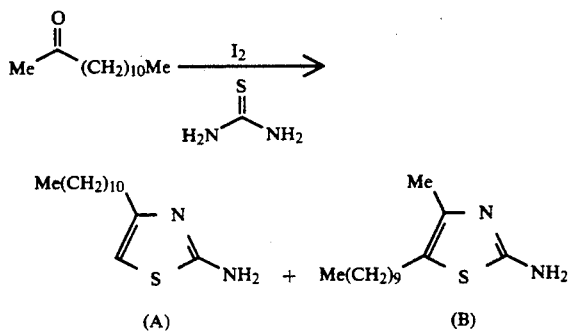

2-Tridecanone (19.3 g, 0.1 mol) and thiourea (15.24 g, 0.2 mol) were stirred at 40° C. until a slurry was obtained. Iodine (25.4 g, 0.1 mol) was added in one portion and the mixture heated at 100° C. for 18 hours, allowed to cool, and diluted with water (50 mL). The aqueous solution was made basic with saturated $NH_4OH$ solution, precipitating a white gum which was partitioned into ethyl acetate (200 mL). The organic layer was washed with saturated $NaHSO_3$, dried with $Na_2SO_4$, concentrated in vacuo to give an oil which was columned on silica gel, eluting with 20, 25, and 50% ethyl acetate in hexanes to yield (A) 4.95 g and (B) 13.5 g.

(b) Preparation of N-[2,6-bis(1-methylethyl)phenyl]-N'-(5-decyl-4-methyl-2-thiazolyl)urea

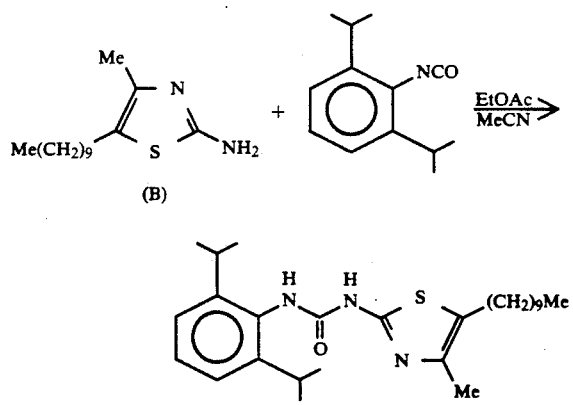

2,6-Diisopropylphenylisocyanate (11.2 g, 0.055 mol) was added to a solution of amine (B) (13.4 g, 0.053 mol) in ethyl acetate (200 mL). The mixture was stirred for 2 hours at room temperature, then acetonitrile (50 mL) added and the mixture refluxed for a further 2 hours, concentrated, and the resulting oil crystallized from acetonitrile (10 mL), filtered, and washed with hexane (200 mL) to give 8.38 g of the urea as a white solid, m.p. 101°–108° C.

EXAMPLE 2

Preparation of N-[2,6-bis(1-methylethyl)phenyl]-N'-(4-undecyl-2-thiazoyl)urea

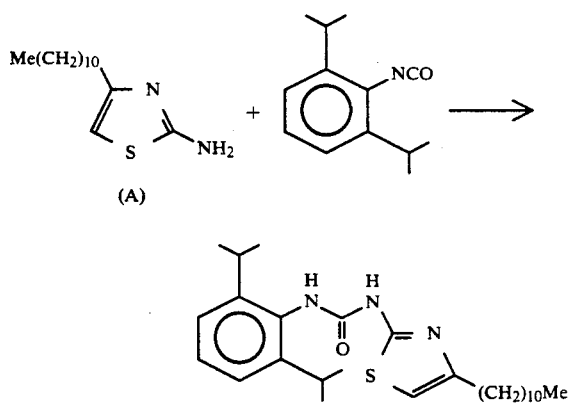

2,6-Diisopropylphenylisocyanate (4.0 g, 0.02 mol) was added to a solution of the amine (A) (4.78 g, 0.019 mol) in ethyl acetate (150 mL) and the mixture refluxed for 18 hours. The precipitate obtained was filtered and the filtrate concentrated and chromatographed on silica gel, eluting with 5% to 10% ethyl acetate in hexanes to give the product 4.57 g as an oil.

Calcd: C, 70.85; H, 9.47; N, 9.18; S, 7.01.
Found: C, 71.42; H, 9.48; N, 8.70; S, 6.17.

EXAMPLES 3 and 4

(a) Preparation of 2-amino-4-methyl-5-pentylthiazole (C) and 2-amino-4-hexylthiazole (D)

When in the procedure of Example 1(a) an appropriate amount of 2 octanone was substituted for 2-tridecanone and the procedure of Example 1(a) is followed the title compounds (C) and (D) were obtained.

(b) When in the procedure of Example 1(b) an appropriate amount of (C) or (D) was substituted for (B) the following respective compounds of Example 3 and 4 were obtained:

EXAMPLE 3

N-[2,6-bis(1-methylethyl)phenyl]-N-(5-pentyl-4-methyl-2-thiazolyl)urea, m.p. 122°-124° C.

EXAMPLE 4

N-[2,6-bis(1-methylethyl)phenyl]-N'-(4-hexyl-2-thiazolyl)urea,

Calcd: e, 68.18; H, 8.58; N, 10.84; S, 8.27.
Found: c, 68.05; H, 8.64; N, 10.84; S, 8.15.

When in the procedures of Example 2 an appropriate amount of 2-amino-4-phenylthiazole, 2-amino-4-methylthiazole or 2-amino-4-tert-butylthiazole is substituted for 2 amino-4-methyl-5-decylthiazole the following respective compounds are obtained:

EXAMPLE 5

N-[2,6-bis(1-methylethyl)phenyl]-N'-(4-phenyl-2-thiazolyl)urea, m.p. 171°-173° C.

EXAMPLE 6

N-[2,6-bis(1-methylethyl)phenyl]-N'-(4-methyl-2-thiazolyl)urea, m.p. 172°-174° C.

EXAMPLE 7

N-[2,6-bis(1-methylethyl)phenyl]-N'-(4-tert-butyl-2-thiazolyl)urea, m.p. 179°-183° C.

EXAMPLE 8

Preparation of N-[2,6-bis(1-methylethyl)phenyl]-N'-(3-dodecyl-5-isoxazolyl)urea (a) Preparation of Phenyl Cyanate Into a 2-L three neck flask equipped with a drop-in funnel, thermometer, and mechanical stirrer was placed phenol (84.3 g, 0.896 mol), cyanogen bromide (100.0 g, 0.944 mol), anhydrous ether (450 mL), and pentane (450 mL). The resulting solution was cooled (0° C.), and while stirring vigorously triethylamine 131.6 mL, 0.944 mol) was added dropwise at a rate not allowing the temperature to rise above 15° C. The resulting slurry was stirred vigorously (1 hour, 0° C.), then filtered through a glass frit. The filter cake was washed with pentane (2×400 mL), and the combined filtrates were concentrated in vacuo, then distilled to yield 94.1 g (88.2%) of phenyl cyanate as a clear liquid, b.p. 76°-79° C., 15 mm.

(b) Preparation of 2-pentadecynenitrile n-BuLi (2.2 M, 24.3 mL, 53.5 mmol) was added dropwise to a cooled (−78° C.) slurry of tetradecyne (10.3 g, 52.7 mmol) in anhydrous ether (60 mL) at a rate not allowing the temperature to rise above −40° C. The resulting slurry was stirred (5 minutes, 70° C.), then phenyl cyanate (6.9 g, 58.0 mmol) was added dropwise at a rate not allowing the temperature to rise above −60° C. The resulting slurry was stirred (45 minutes, −78° C.) then warmed (25° C.). The resulting solution was diluted with ether (140 mL), washed with 1.5 N NaOH (2×100 mL), washed with brine (1×100 mL), then dried (MgSO₄), and concentrated in vacuo. The resulting oil was chromatographed on silica (pentane to 95:5 pentane:ether) to yield 9.0 g (77.8%) of 2-pentadecynenitrile as a pale yellow liquid.

Analysis for $C_{15}H_{25}N$:
Calcd: C, 82.13; H, 11.49; N, 6.39.
Found: C, 82.18; H, 11.74; N, 6.22.

(c) Preparation of 5-amino-3-dodecylisoxazole

A solution of 2-pentadecynenitrile (10.0 g, 45.6 mmol) in ethanol (50 mL) was added to a stirred solution of hydroxylamine hydrochloride (3.8 g, 54.6 mmol) in 2.5 N NaOH (20.0 mL, 50.1 mmol). The resulting mixture was diluted with ethanol (100 mL) and stirred (22 hours, 25° C.). The obtained slurry was concentrated, then partitioned between ethyl acetate (300 mL) and brine (100 mL). The organic layer was dried (MgSO₄), concentrated in vacuo, and chromatographed on silica (95:5 to 70:30 hexane:ethyl acetate) to yield 8.2 g (71.2%) of 5-amino-3-dodecyl-isoxazole as a waxy solid, m.p. 48.5°-49.5° C.

(d) Preparation of N-[2,6-bis(1-methylethyl)phenyl]-N'-(3-dodecyl-5-isoxazolyl)urea A slurry of 5-amino-3-dodecylisoxazole (1.44 g, 5.71 mmol) in acetonitrile (50 mL) was warmed until homogeneous. 2,6-Diisopropylphenylisocyanate (1.22 mL, 5.71 mmol) was then added in one portion and the resulting solution was heated under reflux for 24 hours. The resulting solution was cooled to −20° C. The resulting precipitate was collected by filtration, dissolved in a minimal amount of warm chloroform, and chromatographed on silica (70:30 hexane:ethyl acetate). The product containing fractions were concentrated and the resulting solid was recrystallized from acetonitrile to yield 0.53 g (20.4%) of the title compound as white needles, m.p. 112.5°–114° C.

EXAMPLE 9

Preparation of N-[2,6-bis(1-methylethyl)phenyl]-N'-(5-dodecyl-3-isoxazolyl)urea (a) Preparation of 3-amino-5-dodecylisoxazole A solution of 2-pentadecynenitrile (2.9 g, 13.2 mmol) in ethanol (60 mL) was added to a stirred solution of hydroxylamine hydrochloride (1.1 g, 15.8 mmol) in 1.0 N NaOH (29.1 mL, 29.1 mmol). The resulting mixture was stirred for 16 hours (25° C.). The resulting slurry was filtered and the crystals were washed with cold water and dried in a vacuum oven at 40° C. (24 hours) to yield 2.4 g (71.9%) of 3-amino-5-dodecyl-isoxazole as white platelets; m.p. 79.5°–81° C.

(b) Preparation of N-[2,6-bis(1-methylethyl)phenyl]-N'-(5-dodecyl-3-isoxazolyl)urea A slurry of 3-amino-5-dodecylisoxazole (2.20 g, 8.72 mmol) in acetonitrile (50 mL) was warmed until homogeneous. 2,6-Diisopropylphenyl-isocyanate (1.86 mL, 8.72 mmol) was then added in one portion and the resulting solution was heated under reflux for 6 hours. The resulting solution was cooled (25° C.), concentrated in vacuo, and chromatographed on silica (90:10 to 70;30 hexane:ethyl acetate). The product containing fractions were combined and concentrated to a solid which was washed with cold acetonitrile to yield 0.95 g (23.9%) of the title compound as a white solid, m.p. 101°–107° C.

When in the procedure of Example 8(b) an appropriate amount of dodecyne, tridecyne, pentadecyne, hexadecyne or propadecyne was substituted for tetradecyne, the following respective nitriles were obtained:

tridec-2-ynenitrile;
tetradec-2-ynenitrile;
hexadec-2-ynenitrile;
heptadec-2-ynenitrile; and
butadec-2-ynenitrile.

When in the procedure of Example 8(c) an appropriate amount of tridec-2-ynenitrile, tetradec-2-ynenitrile, hexadec-2 ynenitrile, and heptadec-2 ynenitrile was substituted for 2 mL pentadecynenitrile, the following respective compounds were obtained:

5-amino-3-decylisoxazole;
5-amino-3-undecylisoxazole;
5-amino-3-tridecylisoxazole; and
5-amino-3-tetradecylisoxazole.

When in the procedure of Example 8(d) an appropriate amount of 5-amino-3-decylisoxazole, 5-amino-3-undecylisoxazole, 5-amino-3-tridecylisoxazole or 5-amino-3 tetradecylisoxazole was substituted for 5-amino-3-dodecylisoxazole the following respective compounds were obtained:

EXAMPLE 10

N-[2,6-bis(1-methylethyl)phenyl]-N'-(3-decyl-5-isoxazolyl)urea, m.p. 112°–114° C.

EXAMPLE 11

N-[2,6-bis(1-methylethyl)phenyl]-N'-(3-undecyl-5-isoxazolyl)urea, m.p. 103.5°–104.5° C.

EXAMPLE 12

N-[2,6-bis(1-methylethyl)phenyl]-N'-(3-tridecyl-5-isoxazolyl)urea, m.p. 101°–104° C.

EXAMPLE 13

N-[2,6-bis(1-methylethyl)phenyl]-N'-(3-tetradecyl-5-isoxazolyl)urea, m.p. 104°–106° C.

When in the procedure of Example 9(a) an appropriate amount of 2-tridecynenitrile, 2-tetradecynenitrile, 2-hexadecynenitrile, 2-heptadecynenitrile, or 2-butadecynenitrile was substituted for 2-pentadecynenitrile, the following respective compounds were obtained:

3-amino-5-decylisoxazole,
3-amino-5-undecylisoxazole,
3-amino-5-tetradecylisoxazole, and
3-amino-5-methylisoxazole.

When in the procedure of Example 9(b) an appropriate amount of 3-amino-5-decylisoxazole, 3-amino-5-undecylisoxazole, 3-amino-5-tridecylisoxazole, 3-amino-5-tetradecylisoxazole, or 3-amino 5-methylisoxazole is substituted for 3-amino-5-dodecylisoxazole, the following compounds were obtained:

EXAMPLE 14

N-8 2,6-bis(1-methylethyl)phenyl]-N'-(5-decyl-3-isoxazolyl)urea, m.p. 107°–113° C.

EXAMPLE 15

N-[2,6-bis(1-methylethyl)phenyl]-N'-(5-undecyl-3-isoxazolyl)urea, m.p. 104°–112° C.

EXAMPLE 16

N-[2,6-bis(1-methylethyl)phenyl]-N'-(5-tridecyl-3-isoxazolyl)urea, m.p. 85°–100° C.

EXAMPLE 17

N-[2,6-bis(1-methylethyl)phenyl]-N'-(5-tetradecyl-3-isoxazolyl)urea, m.p. 92°–101° C.

EXAMPLE 18

N-[2,6-bis(1 methylethyl)phenyl]-N'-(5-methyl-3-isoxazolyl)urea, m.p. 203°–204° C.

When in the procedure of Example 9(a) an appropriate amount of 4-dibutylamino-2-butynenitrile or 4-dihexylaminobutynenitrile was substituted for 2-pentadecynenitrile, 3-amino-5-dibutylaminomethylisoxazole, and 3-amino-5-dihexylaminomethylisoxazole were obtained respectively, and when each of these isoxazoles was substituted for 3-amino-5-dodecylisoxazole in the procedure of Example 9(b), the following compounds were obtained:

EXAMPLE 19

N-[2,6-bis(1-methylethyl)phenyl]-N'-[5-[(dibutylamino)methyl]-3-isoxazolyl]urea, m.p. 150°–151° C.

EXAMPLE 20

N-[2,6-bis(1-methylethyl)phenyl]-N'-[5-[(dihexylamino)methyl]-3-isoxazolyl]urea, m.p. 117°–118° C.

5,162,360

EXAMPLE 21

Preparation of N-[2,6-bis(methylethyl)phenyl]-N'-(4-undecyl-2-oxazolyl)urea (a) Preparation of 2-trimethylsilyloxy-1-tridecene A solution of n-butyllithium (12.6 mL, 27.7 mmol, 2.2 M in hexane) was added dropwise via syringe to a cooled (−78° C.) solution of diisopropylamine (4.1 mL, 29 mmol) in dry THF (200 mL). The resulting solution was stirred (15 minutes −78° C.), then a solution of 2-tridecanone (5.0 g, 25 mmol) in dry THF (50 mL) was added dropwise via a drop-in funnel. The resulting mixture was stirred (30 minutes, −78° C.), then a solution of chlorotrimethylsilane (3.5 mL, 28 mmol) in dry THF (40 mL) was added in one portion. The dry ice bath was removed and the resulting mixture was warmed to 10° C., then quenched with saturated sodium bicarbonate (100 mL). Dichloromethane (400 mL) and water (80 mL) were added and the layers were separated. The organic layer was washed with brine (1×200 mL), dried (MgSO4), and concentrated in vacuo to yield 6.7 g (98%) of the title compound as a milky oil which was used without further purification.

Anal. for $C_{16}H_{34}OSi$:
Calcd C, 71.04; H, 12.67.
Found: C, 71.51; H, 12.91.

(b) Preparation of 1-hydroxy-2-tridecanone

3-Chloroperoxybenzoic acid is added in one portion to a cooled (0° C.) solution of 2-trimethylsilyloxy-1-tridecene in hexane (200 mL). The ice bath is removed and the resulting slurry is stirred (4 hours, 25° C.). Ether (200 mL) and 1.5 N HCl (130 mL) are added and the resulting two-phase mixture is stirred vigorously (4.5 hours, 25° C.). The layers are separated and the organic layer is washed with saturated sodium bicarbonate (2×130 mL), washed with brine (1×130 mL), dried (MgSO4), and concentrated in vacuo. The residue is chromatographed on silica (90:10 hexane:ethyl acetate), and concentrated in vacuo. The resulting solid is washed with cold hexane and collected by filtration to yield 1.5 g (29%) of the title compound as white platelets, m.p. 52°–54° C.

(c) Preparation of 2-amino-4-undecyloxazole

To a solution of 1-hydroxy-2-tridecanone (1.0 g, 4.7 mmol) and cyanamide (0.2 g, 5 mmol) in THF (3.0 mL) was added aqueous sodium acetate (2.0 mL, 1.0 N), tetra n-butylammoniumhydroxide (0.6 mL, 0.4 N 0.2 mmol), and sodium hydroxide (0.2 mL, 1.0 N, 0.2 mmol) sequentially. The resulting two-phase mixture was stirred (48 hours, 25° C.). The resulting mixture was taken up in ethyl acetate (200 mL), washed with brine (2×65 mL), dried (MgSO4), and concentrated in vacuo. The residue was chromatographed on silica (pure chloroform to 95:5 chloroform:methanol) and concentrated in vacuo to yield 0.70 g (63%) of the title compound as an off-white powder, m.p. 55°–58° C.

(d) Preparation of N-[2,6-bis(methylethyl)phenyl]-N'-(4-undecyl-2-oxazolyl)urea

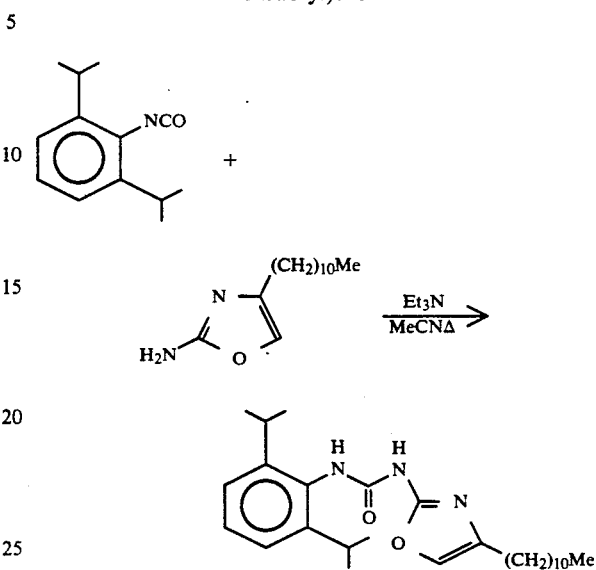

2,6-Diisopropylphenylisocyanate (0.57 g, 0.0028 mol) was added to a refluxing mixture of the oxazole (0.56 g, 0.0024 mol), triethylamine (0.26 g, 0.0026 mol), and acetonitrile (50 mL). The mixture was refluxed for 2.5 hours under $N_2$, allowed to cool, and concentrated in vacuo. The residue was partitioned between ethyl acetate (100 mL) and water (75 mL). The separated organic layer was washed with brine, dried with $Na_2SO_4$, filtered, concentrated, and triturated with acetonitrile to give a yellow solid (0.73 g, 70%) which was dried in vacuo, m.p. 104°–108° C.

Calcd: C, 73.43; H, 9.81; N, 9.51.
Found: C, 73.34; H, 9.72; N, 9.53.

EXAMPLE 22

Preparation of N-[2,6-bis(1-methylethyl)phenyl]-N'-[3-[(dibutylamino)methyl]-1-(phenylmethyl)-1H-pyrazol-5-yl]urea (a) Preparation of 4-dibutylamino-2-butynenitrile n-BuLi (2.2 M, 69.5 mL, 0.153 mol) was added dropwise to a cooled (−78° C.) solution of 3-dibutylaminopropyne (24.9 g, 0.149 mol) in anhydrous ether (175 mL) at a rate not allowing the temperature to rise above −50° C. The resulting solution was stirred (5minutes, −70° C.), then phenyl cyanate (19.6 g, 0.164 mol) was added dropwise at a rate not allowing the temperature to rise above −60° C. The resulting solution was stirred (45 minutes, −78° C.), then warmed (25° C.). The resulting dark brown solution was diluted with ether (250 mL), washed with 3.0 N NaOH (3×170 mL), washed with brine (1×170 mL), then dried (MgSO4), and concentrated in vacuo. The resulting oil was chromatographed on silica (chloroform) to yield 27.0 g (94.4%) of 4-dibutylamino-2-butynenitrile as a brown liquid. $^1H$ NMR (250 MHz, CDCl3): δ 3.53 (s, 2H), 2.46 (t, 4H), 1.36 (m, 8H), 0.92 (t, 6H).

(b) Preparation of 5-amino-3-(dibutylamino)methyl]-1-(phenylmethyl)-1H-pyrazole A solution of 4-dibutylamino-2-butynenitrile in ethanol (10 mL) was added to a stirring solution of benzylhydrazine dihydrochloride (3.0 g, 15.4 mmol) and 3.0 N NaOH (5.00 mL, 15.4 mmol) in ethanol (50 mL). The resulting solution as stirred (2 hours, 25° C.), then concentrated. The residue was taken up in ethyl acetate (250 mL), washed with brine (3×90 mL), then dried (MgSO$_4$) and concentrated in vacuo. The resulting oil was chromatographed on silica (80:20 hexane:ethyl acetate) to yield 0.70 g (14.5%) of 5-amino-3-[(dibutylamino)methyl]-1-(phenylmethyl)-1H-pyrazole as an orange oil. $^1$H NMR (250 MHz, CDCl$_3$ δ 7.22 (m, 6H), 4.56 (s, 2H), 4.00 (br s, 2H), 2.30 (m, 4H), 1.34 (m, 8H), 0.90 (t, 6H).

(c) Preparation of N-[2,6-bis(1-methylethyl)phenyl]-N'-3-[(dibutylamino)methyl]-1-(phenylmethyl)-1H-pyrazol-5-yl]urea A solution of 5-amino-3-[(dibutylamino)methyl]-1-(phenylmethyl)-1H-pyrazole (0.70 g, 2.2 mmol), 2,6-diisopropylphenylisocyanate (0.48 mL, 2.2 mmol), and cuprous iodide (cat) in acetonitrile was heated to reflux for 16 hours. The resulting solution was cooled (25° C.), concentrated in vacuo, and chromatographed on silica (90:10 hexane:ethyl acetate). The product containing fractions were combined and concentrated in vacuo. The resulting oil was crystallized from hexane to yield 0.40 g (34.7%) of the title compound as a white powder, m.p. 149°–151.5° C.

EXAMPLE 23

Preparation of N-[2,6-bis(1-methylethyl)phenyl]-N'-(1-undecyl-1H-pyrazol-5-yl)urea (a) Preparation of 5 or 3-amino-1-undecyl-1H-pyrazole A solution of 3-aminopyrazole (10.0 g, 0.120 mol) in THF (50 mL) was added dropwise over 15 minutes to a cooled (0° C.) slurry of hexane washed sodium hydride (4.82 g, 0.126 mol, 60% oil dispersion) in THF (300 mL). The ice bath was removed and the resulting slurry was stirred (1 hour). Undecylbromide (26.86 g, 0.114 mol) was then added in one portion, and the resulting slurry was heated to reflux for 48 hours. The resulting slurry was cooled (25° C.) and concentrated. The residue was taken up in ethyl acetate (450 mL), washed with saturated sodium bicarbonate (1×150 mL), washed with brine (1×150 mL), then dried (MgSO$_4$) and concentrated in vacuo. The resulting oil was chromatographed on silica (99:1 chloroform:methanol) to yield 5.5 g (20.3%) of 5 or 3-amino-1-undecyl-1H-pyrazole as a yellow oil. $^1$H NMR (90 MHz, DMSO) δ 7.15 (d, 1H), 5.31 (d, 1H), 4.30 (br s, 2H), 3.73 (t, 2H), 1.67 (p, 2H), 1.27 (s, 16H), 0.87 (t, 3H).

(b) Preparation of N-[2,6-bis(1-methylethyl)phenyl]-N'-(1-undecyl-1H-pyrazol-5 or 3-yl)urea A solution of 3-amino-1-undecyl 1H pyrazole (3.7 g, 15.6 mmol) and 2,6-diisopropylphenylisocyanate (3.15 mL, 15.6 mmol) in acetonitrile (100 mL) was heated under reflux for 5 hours, then cooled (25° C.) and concentrated in vacuo to yield 7.0 g (100%) of the title compound as a yellow oil.

Analysis for $C_{27}H_{44}N_4O$:
Calcd: C, 73.59; H, 10.06.
Found: C, 73.87; H, 10.36.

EXAMPLE 24

Preparation of N-[2,6-bis(1-methylethyl)phenyl]-N'-[3-dodecyl-1-(2-pyridyl)-1H-pyrazol-5-yl]urea When in the procedure of Example 22(b) an appropriate amount of 2-pyridylhydrazine as substituted for benzylhydrazone and the general procedure of steps (b) and (c) of Example 22 followed, the title compound was obtained.

EXAMPLE 25

N-[2,6-Bis(1-methylethyl)phenyl]-N'-(1-dodecyl-1H-imidazol-4-yl)urea monohydrochloride (a) Tetrabutylammonium hydroxide (22 mL of 0.4 M solution, 0.0088 mol) was treated with sodium hydroxide (4.64 g, 0.116 mol) followed by 4-nitroinidazole (1.0 g, 0.0088 mol). The mixture was then diluted with chloroform (28 mL) and stirred for 2 hr at room temperature. The organic layer was then separated and dried with MgSO$_4$. After filtration the chloroform solution was diluted with diethylether (200 mL) and the resulting brown solid filtered, washed with ether and dried in vacuo at 59° C. overnight to give 4-nitro-tetrabutylammonium imidazole Yield 5.9 g, 67%

(b) To a solution of the 4-nitro-tetrabutyl ammonium nitroimidazole (0.5 g, 1.4 mmol) in dimethyl formamide (10 mL) was added the dodecylbromide (0.35 g, 1.4 mmol). The mixture was stirred at room temperature for 18 hr, concentrated in vacuo, diluted with water (50 mL) and extracted with 1:1 ethylacetate/hexane (100 mL) twice. The combined organic layers were washed with saturated NaCl, dried MgSO$_4$, filtered and concentrated in vacuo to yield 1-dodecyl-4-nitroimidazole which was used immediately in the next reaction.

(c) The 1-dodecyl-4-nitroimidazole (1.5 g, 5.3 mmol) was treated with 5% Pd/c in methanol at 50 psi of hydrogen, for 6 hr at 22°–28° C. in a Parr apparatus. The crude reaction mixture containing 1-dodecyl-4-aminoimidazole was concentrated and used immediately in the next step without purification.

(d) To a solution of 1-dodecyl-4-aminoimidazole in ethyl acetate (5 mL) was added the isocyanate (0.64 g, 3.2 mmol). The resulting mixture was stirred for 3 hr at room temperature, diluted with water (10 mL) and stirred for 30 min. The organic layer was separated and washed with saturated NaHCO$_3$, brine and dried (MgSO$_4$). The mixture was filtered, concentrated and columned on silica gel eluting with 10, 20, 30, 40, and 60% ethyl acetate in hexanes. The brown oil obtained was treated with saturated ethereal HCl, concentrated, dissolved in methanol and water added. The mixture was concentrated in vacuo and then lyophilized overnight to yield 0.25 g, 16% of the title compound.

CHN found: 68.16, 9.81, 11.24.
CHN expected: 68.47, 9.65, 11.41.

FLOW CHART

Scheme I:

-continued
FLOW CHART
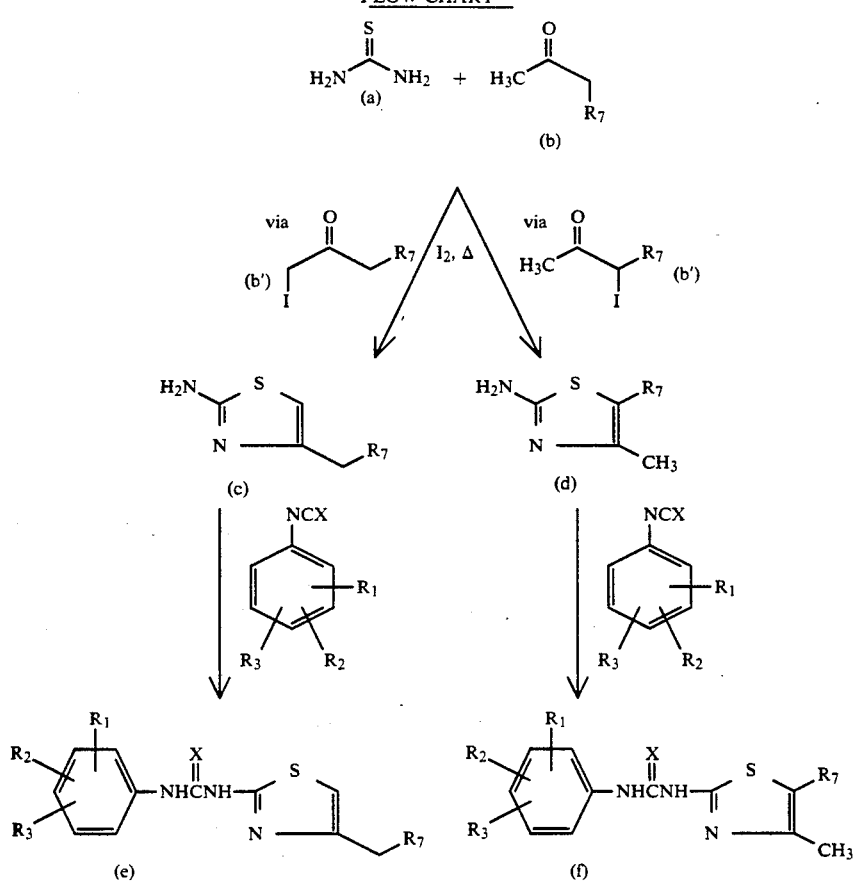
Scheme II:
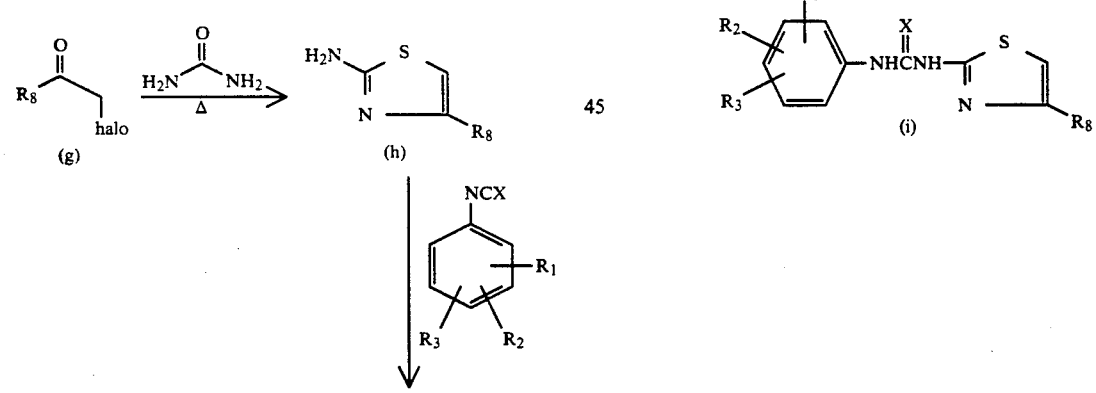
Scheme III:
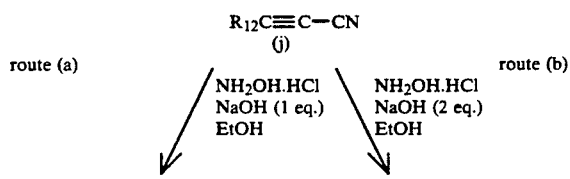

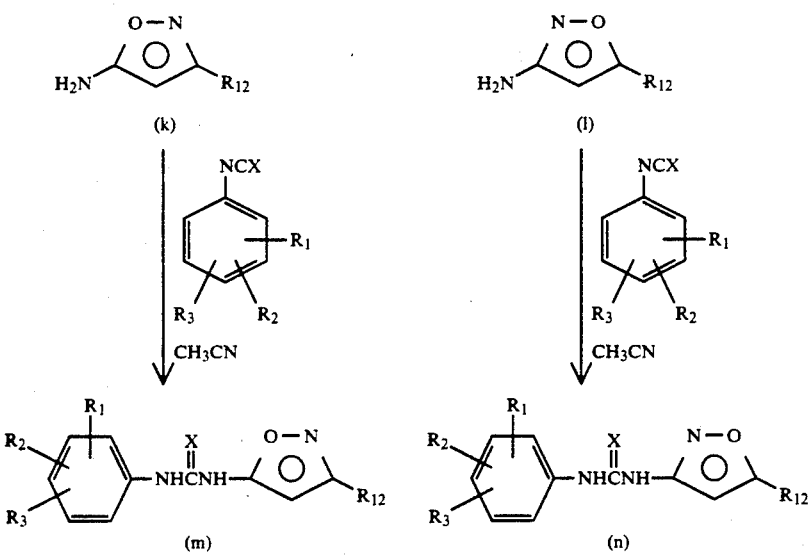
Scheme IV:
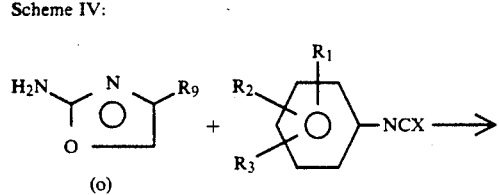
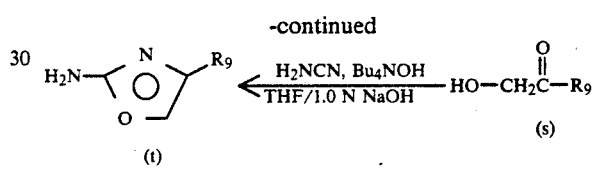
Scheme V:
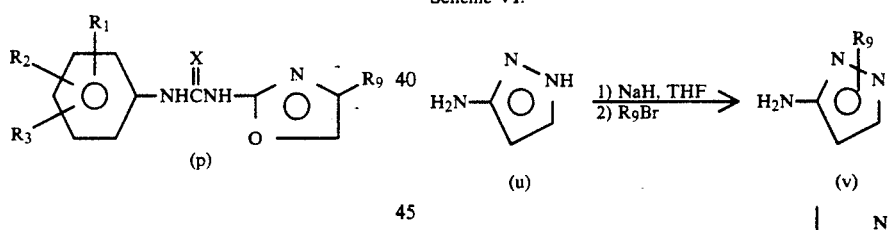
Scheme VI:
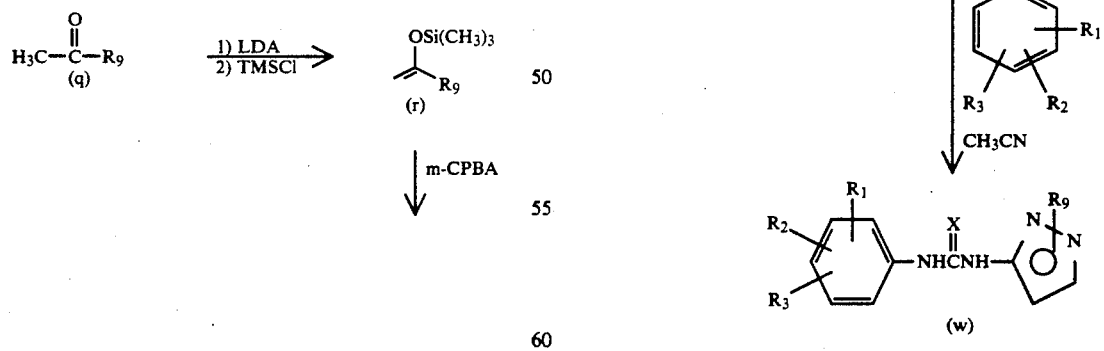
Scheme VII:

-continued

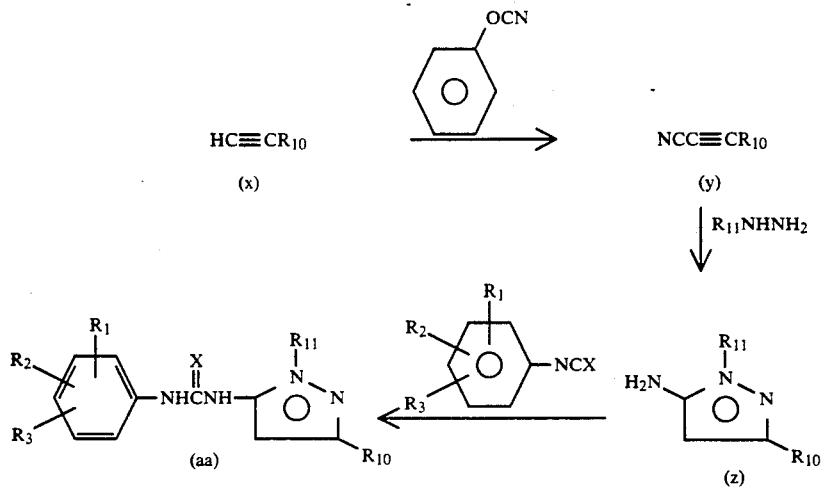

Scheme VIII:

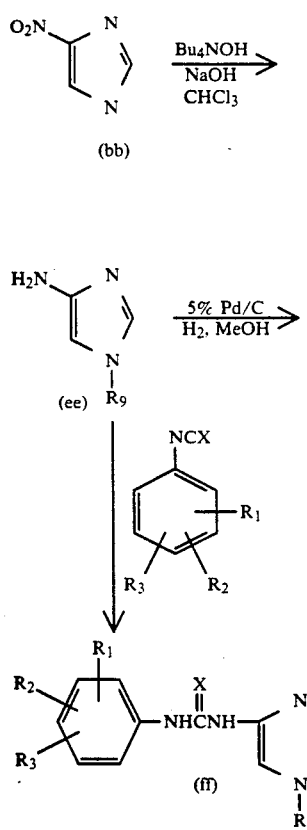

We claim:
1. A compound of the formula

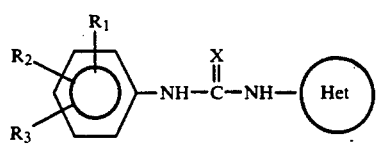

wherein
X is oxygen or sulfur;

wherein each of $R_1$, $R_2$, and $R_3$ is the same or different and is selected from
hydrogen,
fluorine,
chlorine,
bromine,
a straight or branched alkyl group having from one to six carbon atoms,
a straight or branched alkoxy group having from one to six carbon atoms,
benzoyl which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms,
benzyl which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms,
phenyl which is unsubstituted or is substituted with from one to three substituents selected from fluorine, chlorine, bromine, iodine, a straight or branched alkyl group having from one to six carbon atoms, or a straight or branched alkoxy group having form one to six carbon atoms,
$NR_4R_5$ wherein each of $R_4$ and $R_5$ is the same or different and is hydrogen, a straight or branched alkyl group having from one to four carbon atoms or $-NR_4R_5$ taken together from a monocyclic heterocyclic group selected from pyrrolidino, piperidino, piperazine, or piperazine substituted on the 4-position with a straight or branched alkyl group having form one to four carbon atoms;
$-COR_6$ wherein $R_6$ is hydroxy, a straight or branched alkoxy group having from one to six carbon atoms, benzyloxy which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms, or $R_6$ is $-NR_4R_5$ wherein $R_4$ and $R_5$ have the meanings defined above;
wherein Het is selected from

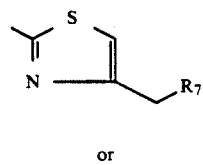

or

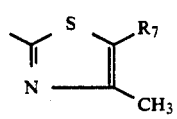

wherein $R_7$ is straight or branched alkyl having from 9 to 14 carbon atoms; and pharmaceutically acceptable salts and isomers thereof.

2. A method for treating hypercholesterolemia and atherosclerosis in a patient in need thereof which comprises administering to said patient an effective amount of a compound of claim 1 together with a pharmaceutically acceptable carrier.

3. A pharmaceutical composition comprising a compound of claim 1 and a pharmaceutically acceptable carrier.

4. A compound of claim 1 which is N-[2,6-bis(1-methylethyl)phenyl]-N'-(5-decyl-4-methyl-2-thiazolyl)urea or a pharmaceutically acceptable salt thereof.

5. A compound of claim 1 which is N-[2,6-bis(1-methylethyl)phenyl]-N'-(4-undecyl-2-thiazolyl)urea or a pharmaceutically acceptable salt thereof.

* * * * *

UNITED STATES PATENT AND TRADEMARK OFFICE
CERTIFICATE OF CORRECTION

PATENT NO. : 5,162,360
DATED : November 10, 1992
INVENTOR(S) : Creswell, et. al.

It is certified that error appears in the above-indentified patent and that said Letters Patent is hereby corrected as shown below:

Column 22, line 55, change "piperazine, or Piperazine" to --piperazino, or piperazino--.

Signed and Sealed this

Eleventh Day of January, 1994

Attest:

BRUCE LEHMAN

Attesting Officer     Commissioner of Patents and Trademarks